United States Patent [19]

Jansen

[11] Patent Number: 5,681,573
[45] Date of Patent: Oct. 28, 1997

[54] PROCESS TO PREPARE PHARMACEUTICAL COMPOSITIONS CONTAINING VECURONIUM BROMIDE AND COMPOSITIONS PRODUCED THEREBY

[75] Inventor: Frans Herwig Jan Jansen, Oud Turnhout, Belgium

[73] Assignee: N.V. Inpharm, Oud Turnhout, Belgium

[21] Appl. No.: 495,579

[22] PCT Filed: Feb. 8, 1994

[86] PCT No.: PCT/EP94/00358

§ 371 Date: Aug. 8, 1995

§ 102(e) Date: Aug. 8, 1995

[87] PCT Pub. No.: WO94/17808

PCT Pub. Date: Aug. 18, 1994

[30] Foreign Application Priority Data

Feb. 8, 1993 [GB] United Kingdom ............... 9302455

[51] Int. Cl.⁶ ........................................ A61K 9/19
[52] U.S. Cl. ............................. 424/400; 424/489
[58] Field of Search ........................... 424/400, 489

[56] References Cited

U.S. PATENT DOCUMENTS

| 3,553,212 | 1/1971 | Hewett et al. ............... 540/96 |
| 5,030,633 | 7/1991 | Williams ..................... 514/231.5 |

FOREIGN PATENT DOCUMENTS

| 0008824 | 3/1980 | European Pat. Off. . |
| 0 008 824 | 4/1982 | European Pat. Off. . |
| 0287150 | 10/1988 | European Pat. Off. . |
| 0571012 | 11/1993 | European Pat. Off. . |
| 1138605 | 1/1969 | United Kingdom . |

OTHER PUBLICATIONS

Buckett et al., "Pancuronium Bromide and Other Steriodal Neuromuscular Blocking Agents Containing Acetylcholine Fragments", Journal of Medicinal Chemistry, vol. 16, No. 10 (1973) pp. 1116–1124.

*Primary Examiner*—Amy Hulina
*Attorney, Agent, or Firm*—Foley & Lardner

[57] ABSTRACT

The invention relates to a process for preparing a pharmaceutical preparation having neuromuscular blocking activity in a vial by dissolving vecuroniumbromide or an analogue thereof in water saturated with carbondioxide or an organic solvent, filling the solution thus obtained into the vial to provide therein the required unit dosage form of vecuronium bromide or an analogue thereof, removing the solvent, i.e. water or organic solvent in the vial by lyophilization or evaporation, and hermetically closing the vial. The invention also relates to a method of preparing an aqueous injection solution starting from said vial by dissolving the contents of the vial either in an amino acid solution of sufficient concentration so as to obtain a final physiological pH or in a pharmaceutically acceptable buffer system of pH 7 to 7.4.

3 Claims, No Drawings

PROCESS TO PREPARE PHARMACEUTICAL COMPOSITIONS CONTAINING VECURONIUM BROMIDE AND COMPOSITIONS PRODUCED THEREBY

This invention relates to a process for preparing a pharmaceutical preparation having neuromuscular blocking activity. The invention particularly relates to a process for preparing such a preparation containing as neuromuscular blocking agent a 16beta-monoquaternary ammonium derivative of a 2beta, 16beta-bis-piperidino-3alfa, 17beta-dihydroxy-5alfa-androstane-3alfa, 17beta-diacylate.

From British Patent Nr. 1 138 605 it is known that the 2beta, 16beta-bisquaternary ammonium derivatives of 2beta, 16beta-bis-piperidino-3alfa. 17beta-dihydroxy-5alfa-androstane-3alfa, 17beta-diacylates are highly active neuromuscular blocking agents. An example of such a compound is pancurontumbromide (2beta, 16beta-bis-piperidino-5alfa-androstane-3alfa, 17beta-diol 3alfa, 17beta-diacetate 2beta, 16beta-dimethobromide).

In J. Med. Chem. 16, 1116 (1978) it is disclosed that not only such bisquaternary derivatives, but also the corresponding 16-mono-quaternary derivatives are interesting neuromuscular blocking agents. These mono-quaternary derivatives are even more interesting than the corresponding bis-quaternary compounds because of their quicker onset and shorter duration of action, thus offering under most surgical conditions pronounced advantages, and because of their lack of cardiovascular side-effects. A well-known example of a mono-quaternary compound is vecuroniumbromide (2beta, 16beta-bis-piperidino-5alfa-androstane-3alfa, 17beta-diol 3alfa, 17beta-diacetate 16beta-methobromide), hereinafter referred to as "VB".

Generally, the quaternarizing group in the abovementioned androstane compounds is an alkyl, alkenyl or alkynyl group of up to 4 carbon atom, of which the methyl group is preferred. The counterion for the positive quaternary group may be any pharmaceutically acceptable organic or inorganic anion, such as methylsulphate, p-toluene-sulphonate and especially the halides such as chloride, bromide and iodide, of which bromide is preferred. The acyl group in 3alfa- and 17beta-position is derived from a lower aliphatic carboxylic acid having 1–6 carbon atom and is preferably the acetyl group.

The present invention is described herein with respect to VB. However, it should be noted that in the following disclosure any of the abovementioned 16-mono-quaternary analogues of VB may be substitited for VB without departing from the scope of the present invention.

According to the disclosure of EP-A-008824 VB decomposes almost immediately when dissolved in water and hence cannot be used in aqueous injection preparations. Neuromuscular blocking agents are mainly used in surgical treatments and are administered through injection of their aqueous solution. For making stable injection preparations of VB it is suggested in EP-A-008824 to convert VB into a pharmaceutically acceptable acid addition salt thereof by reacting VB with a pharmaceutically acceptable organic or inorganic acid, preferably a water soluble acid, e.g. hydrochloric acid, acetic acid, fumaric acid, citric acid.

According to the "Repertorium" (a review of information texts of pharmaceutical specialité's registered in the Netherlands, edited by Nefarma, the Dutch Pharmaceutical Manufactures Association) the preparation of VB (Norcuron®) consists of a vial containing a lyophilized mixture of the acid addition salt of VB (4 mg or 10 NaCl (0.15 mmol), mannitol (24.5 mg) and a citrate or phosphate buffer. For obtaining an injectable solution the contents of the vial should be dissolved in water for injection purposes (1 ml or 5 ml) giving an isotonic injection solution having a pH of 4. The injection solution is stable for 24 hours at room temperature in the light.

It is an object of the present invention to provide a new method for preparing stable pharmaceutical preparations of VB for injection purposes.

The present invention comprises a method for preparing a stable pharmaceutical preparation containing VB characterized by the steps of (a) dissolving VB in water saturated with carbondioxide or in an organic solvent, (b) filling the solution thus obtained into containers, e.g. vials, to provide in each container the required unit dosage form of VB, (c) removing the solvent, i.e. water or organic solvent, from each container by lyophilization or evaporation, and (d) hermetically closing the container.

The special method according to the invention makes the extra step of first converting VB into an acid addition salt thereof superfluous.

When in step (a) carbondioxide saturated water is used as the solvent, the temperature thereof should be within the range of from 0° C. to 25° C. and is preferably normal room temperature. Despite the presence of water VB surprisingly appears to be stable within the said temperature range, i.e. hydrolysis of VB to the corresponding 3-alfa-hydroxy compound does not substantially take place, as will be shown in the examples which will follow hereinafter. The pH of the carbondioxide saturated aqueous solution of VB is about 7.0, whereas the pH of an carbondioxide free aqueous solution is within the range of from 8.5 to 9.5.

When in step (a) an organic solvent is used for dissolving VB, said solvent can be selected from the group consisting of dichloromethane, choroform, acetone, ethanol, acetonitrile, and the like. In step (c) the organic solvent is removed by evaporation without leaving any trace thereof.

From an aqueous solution of VB obtained in step (a) water is preferably removed by lyophilization or freeze-drying at a temperature of below −25° C., e.g. −30° C. Removal of water in this way in the form of ice can be performed in some hours, e.g 5 hours.

A big advantage of filling the vials with VB in the form of a solution thereof (step (a)) is that the solution can be provided easily in sterilized form, e.g. by simple filtration through an absolute filtersystem (microporous filter, e.g. a Millipore® filter, such as Millidisk 0.22 μm hydrophilic filter) under nitrogen atmosphere. A further advantage of this way of filling the vials is that an accurate dosage in the vial can be provided, e.g. each vial can be filled with a 1 ml aliquot of a solution containing 10 mg VB for providing vials each containing 10 mg VB. Filling of the vials with VB in powder form is difficult. Even micronized VB has poor theological properties (poor free-flowing characteristics), so that filling each vial with the exact amount of VB, using e.g. the "screw filling" technique, is impossible. The required amounts of VB in the vials are not within the 95% confidence limit. Moreover, sterilization of VB in the solid form, e.g. a powder, my present problem. It will be necessary to sterilize with e.g. gamma-rays. All these problem with filling the vials with VB powder are avoided by filling the vials with a solution of VB and then removing the solvent by lyophilization or evaporation according to methods well-known for a person with average skill in the art of pharmaceutical techniques.

Before the lyophilization or evaporation step and for ease of further operation each vial may receive a stopper cap, usually of a synthetic material, that is placed on the top of the vial in a skew way, but does not close the vial. The vials are then quickly deep frozen by passing on a cold plate in a precooled lyophilization machine (-30° C.). Freeze drying commences immediately and after ascertaining complete evaporation of the liquid each vial is closed hermetically with the cap and the vial cap is fixed with a metallic ring-like cap in order to protect it from accidental opening The vials obtained by the method according to the present invention and each exactly containing the required amount of VB, e.g. 10 mg, can be used in clinical practice to produce skeletal muscular paralysis during surgical operations. Just prior to the use the vial is opened, the required amount of aqueous injection solution for dissolving the VB is added, e.g. 1 ml sterile water containing sodium chloride in a sufficient amount so as to ascertain isotonicity with human plasma, and the VB solution is then injected intravenously with a syringe. A VB solution, containing e.g. 10 mg/ml, can also be administered by infusion.

The aqueous solution of VB for injection obtained by the method of reconstitution as described hereinabove can be checked for its contents of VB and for its pH. The contents of VB is within the confidence limit accepted for this purpose.

When according to the invention water saturated with carbondioxide has been used as the solvent for preparing the VB preparation, the method of reconstitution as described hereinabove results in an aqueous solution of VB having a pH slightly exceeding the value 9 indicating that during the freeze drying step all carbondioxide has been removed.

Also, when according to the invention an organic solvent has been used as the solvent for preparing the VB preparation, the method of reconstitution as described hereinabove results in an aqueous solution of VB having a pH slightly exceeding the value 9 indicating the presence of pure VB in the solution.

The aqueous injection solution may be sterile water or physiological saline.

Prior to lyophilization of the VB solution of the present invention other pharmaceutical excipients may be added to obtain a consistent powder after lyophilization.

The powder, obtained by lyophilization of a VB solution in carbondioxide saturated water, may also be reconstituted prior to injection by dissolving the powder under aseptic conditions in a buffered solution having a physiological pH of 7 to about 7.4. Preferred buffer system are phosphate buffers, but any pharmaceutical acceptable buffer system can be used. Also, the lyophilized powder of VB can be dissolved in solutions of suitable amino acids such as glycine, L-serine or any other pharmaceutically acceptable amino acid the like, having a concentration so that the pH of the resulting injection solution does not exceed 7.5, e.g. 0.15M resulting in a pH of 7.45.

The invention will be illustrated by the following non-limiting examples.

EXAMPLE 1

Stability of VB solutions with and without carbondioxide

Four solution were prepared as follows:

(1) 10 mg VB/ml carbondioxide free water, stored at 20° C., pH 9.0–9.5.

(2) As (1), but stored at 4° C.

(3) 10 mg VB/ml water saturated with carbondioxide, stored at 20° C., pH 7.0. (The carbondioxide saturated water was obtained by slowly adding solid carbondioxide to demineralized water, until the pH of the solution reached a value between 3.5 and 4.5.)

(4) As (3), but stored at 4° C.

From these solutions TLC-analysis was performed immediately after the preparations were made, after two hours, four hours, eight hours, 1 day and further every day.

Next to these solutions, solutions containing 5, 10, 20 and 50 mg VB, respectively, in 100 ml dichloromathane were prepared and spotted next to the above aqueous sample solutions. These dichloromethane solutions had VB concentrations of 0.5%, 1%, 2% and 5%, respectively, of the aqueous sample solutions. Intensities of present secondary spots were compared to these comparison solutions. The detection limit was 0.5%

The results are summarized in Table 1 below.

TABLE I

| Lapsed time | Without carbondioxide | | With carbondioxide | |
|---|---|---|---|---|
| | 4° C. | 20° C. | 4° C. | 20° C. |
| | (% VB present in the solution) | | | |
| 0 hr | 100 | 100 | 100 | 100 |
| 2 hr | 70 | 60 | >99 | >99 |
| 4 hr | 30 | 20 | >99 | >99 |
| 8 hr | 20 | 10 | >99 | >99 |
| 1 day | <10 | <10 | >98 | >98 |
| 2 days | <10 | <10 | >98 | >98 |
| 3 days | <10 | <10 | >98 | >98 |
| 5 days | <10 | <10 | >98 | >98 |
| 9 days | <10 | <10 | >98 | >98 |

From these results it is clear that carbondioxide containing aqueous solutions of VB are very stable for at least 9 days.

EXAMPLE 2

Preparation of 1 ml vials each containing 10 mg VB a) Preparation with carbondioxide saturated water as the solvent To sterile water about 30 g of carbondioxide was added in the form of carboglace, with continuous stirring (500 rpm). Under sterile conditions 10 g of VB was dissolved in 1000 ml of the water saturated with carbondioxide gas. Immediately after the dissolution the solution was passed under nitrogen atmosphere through an absolute filtering system, i.e. filtered through a Millipore™ filter (Millidisk 0.22 μm hydrophilic filter). The filling of the vials with the filtered solution was performed immediately thereafter and each vial was accurately filled with 1 ml of the solution. Each vial received a synthetic stopper cap that was placed in a skew way on the top of the vial, but did not close the vial. The vials were quickly frozen by passing on a cold plate in a precooled lyophilization machine (-30° C.). Freeze drying commenced immediately and after ascertaining total evaporation of the liquid, the vials were closed hermetically and the vial cap was fixed with a metallic ring-like cap in order to protect it from accidental opening.

After the freeze drying process the amount of VB in the vial was checked by dissolving the contents of the vial in water, whereafter the amount of VB in the solution was determined. An amount of almost exactly 10 mg was found.

In addition the pH of the solution was measured and found to be slightly above 9, indicating that the vial did not contain any carbondioxide, but only pure VB.

b) Preparation with acetonitrile as the solvent

To an accurately weighed portion of VB (10 g) was added acetonitrile and dissolved with the aid of a short duration of ultrasonic waves. Acetonitrile was added until the solution reached a final volume of 1 liter. The solution obtained in this way was passed through an absolute filter of 0.2 μm pore size for sterilization.

The filter system used was a Sartorius PTFE filter system (SM11807) of 0.2 μm pore size, pre-autoclaved at 134° C.

After the filtration step an accurately measured volume of 1 ml of that solution of VB was transferred to a vial and lyophilized at −30° C., after which the vial was hermetically closed.

Analysis of the VB in the vial showed clearly that the amount of remaining acetonitrile was well below the 100 ppm level.

The gas chromatographic conditions used were as follows: stationary phase: Chromosorb 80–100; carrier gas: helium; flow: 30 ml/min; temperature: 150° C.

EXAMPLE 3

Stability of aqueous injectable VB solutions after reconstitution from lyophilised carbondioxide saturated aqueous VB solutions The following solutions (10 ml) were prepared from 1 mg VB which was obtained by lyophilisation of a carbondioxide saturated aqueous solution of VB according to the method of Example 2a)

a) Phosphate buffer, pH 7.4 b) L-serine, 0.15M c) Glycine, 0.15M d) Water

The results of the stability determinations are summarized in Table 2 below

TABLE 2

| Solution Time (hr) | a) | b) | c) | d) |
|---|---|---|---|---|
| | (% VB present in the solution) | | | |
| 0 | 100 | 100 | 100 | 100 |
| 1 | 100 | 100 | 100 | 60 |
| 2 | 100 | 100 | 100 | 30 |
| 4 | 98 | 98 | 98 | 20 |
| 8 | 97 | 95 | 95 | 10 |

The results indicate an excellent stability with solutions a), b) and c) according to the invention.

I claim:

1. A method for preparing a stable pharmaceutical preparation containing vecuronium bromide comprising:

dissolving vecuronium bromide in water saturated with carbon dioxide to obtain a solution; and lyophilizing the solution to provide a stable pharmaceutical preparation of vecuronium bromide.

2. The method as claimed in claim 1, wherein, prior to lyophilization, the solution is filled into one or more containers such that each container holds an effective unit dosage of vecuronium bromide.

3. The method as claimed in claim 2, wherein, after lyophilization, another container holding an effective amount of a carrier for an injectable formulation is combined into a kit with each of the one or more containers holding effective unit dosages of vecuronium bromide.

* * * * *